United States Patent [19]

Magami et al.

[11] Patent Number: 4,466,975
[45] Date of Patent: Aug. 21, 1984

[54] MICROBICIDAL/MICROBISTATIC COMPOSITIONS FOR INDUSTRIAL USE

[75] Inventors: Masato Magami; Toshio Sato, both of Nakatsu; Sakae Katayama, Kobe; Osamu Umekawa, Kaizuka, all of Japan

[73] Assignees: Yoshitomi Pharmaceutical Industries, Ltd.; Katayama Chemical Works Co., Ltd., both of Osaka, Japan

[21] Appl. No.: 364,978

[22] Filed: Apr. 2, 1982

[30] Foreign Application Priority Data

Apr. 8, 1981 [JP] Japan ................................. 56-53652

[51] Int. Cl.$^3$ .................... A01N 43/78; A01N 43/80; D21H 5/22; C09D 5/16
[52] U.S. Cl. .................................... 424/270; 424/277; 162/161; 106/18.32
[58] Field of Search ................ 424/270, 277; 162/161; 106/18.32

[56] References Cited

U.S. PATENT DOCUMENTS

| | | | |
|---|---|---|---|
| 3,970,755 | 7/1976 | Gazzard et al. | 424/270 |
| 4,062,947 | 12/1977 | Law | 424/270 |
| 4,289,581 | 9/1981 | Katayama et al. | 424/277 |
| 4,334,957 | 6/1982 | Katayama et al. | 424/277 |

Primary Examiner—Jerome D. Goldberg
Assistant Examiner—Freda L. Abramson
Attorney, Agent, or Firm—Hubbell, Cohen, Stiefel & Gross

[57] ABSTRACT

A microbicidal/microbistatic compositions for industrial use, which comprises 4,5-dichloro-1,2-dithiol-3-one and 1,2-benzisothiazolin-3-one, and a method of killing or inhibiting the growth of microbes, which comprises adding 4,5-dichloro-1,2-dithiol-3-one and 1,2-benzisothiazolin-3-one simultaneously or at intervals to a system to be controlled microbicidally/microbistatically.

5 Claims, 4 Drawing Figures

MICROBICIDAL/MICROBISTATIC COMPOSITIONS FOR INDUSTRIAL USE

BACKGROUND OF THE INVENTION

1. Field of the Invention

The present invention is concerned with microbicidal/microbistatic compositions for industrial use which comprise 4,5-dichloro-1,2-dithiol-3-one and 1,2-benzisothiazolin-3-one and with a method of killing and/or inhibiting microbes by using these compositions.

2. Description of the Prior Art 4,5-Dichloro-1,2-dithiol-3-one which has the chemical formula:

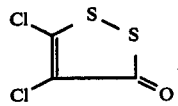

is known to have a strong microbicidal/microbistatic activity, especially against Gram negative bacteria (cf. Japanese Patent Publication No. 14294/1977).

On the other hand, 1,2-benzisothiazolin-3-one having the chemical formula of

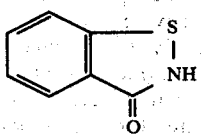

is also known to show a good microbicidal/microbistatic activity, especially against Gram positive bacteria (cf. Japanese Patent Publication No. 7999/1963).

Microbicidal/microbistatic compositions comprising 4,5-dichloro-1,2-dithiol-3-one and a haloacetic acid ester are also known (cf. published British patent specification No. 2,052,989).

The invention is based on the discovery that when the above-mentioned two types of active ingredients are used for various industrial purposes requiring a microbicidal/microbistatic treatment (especially in papermaking process water), they produce a synergistically potentiated microbicidal/microbistatic activity, while retaining their respective microbicidal spectra, and also sustain their activities.

SUMMARY OF THE INVENTION

The present invention provides a microbicidal/microbistatic composition comprising 4,5-dichloro-1,2-dithiol-3-one and 1,2-benzisothiazolin-3-one.

The present invention also provides a method of killing or inhibiting the growth of microbes, which comprises adding 4,5-dichloro-1,2-dithiol-3-one and 1,2-benzisothiaxolin-3-one simultaneously or at intervals to a system to be controlled microbicidally/microbistatically.

The compositions and method according to the present invention are particularly useful for controlling slime in process water of papermaking and industrial cooling water and also for the microbicidal/microbistatic treatment of various industrial materials, such as heavy oil sludges, cutting oils, textile oils and the like.

BRIEF DESCRIPTION OF THE DRAWING

Similarly.

DESCRIPTION OF THE PREFERRED EMBODIMENT

Figure 1:
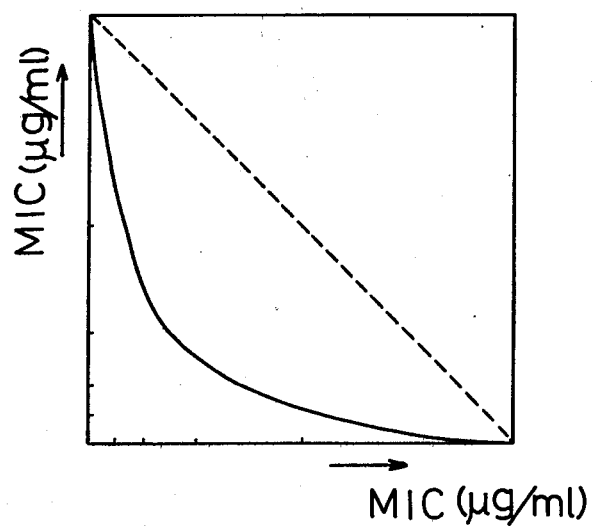
FIG. 1 of the accompanying drawings is a sample of a graph for showing a synergistic effect on minimum inhibitory concentrations (MIC, $\mu g/ml$) in accordance with the two-dimensional dilution method.

The active ingredients are preferably used in the form of a liquid preparation, without limitation thereto. Depending upon the kind of materials to be treated, they may be used in the form of a powder of liquid preparation.

The solvents to be used in the or liquid preparation are preferably organic solvents and especially substantially anhydrous organic solvents because 4,5-dichloro-1,2-dithiol-3-one tends to hydrolyze in the presence of water.

The organic solvents for the liquid composition are preferably hydrophilic solvents which can dissolve the active ingredients, are miscible with water, can give storable, stable compositions when used with an appropriate surfactant and can promote the dispersion of the active ingredients in water when the composition is added to water systems. Examples of such organic solvents include amides, such as dimethylformamide and diethylformamide; glycols, such as ethylene glycol, propylene glycol, diethylene glycol and dipropylene glycol; glycol ethers, such as methyl cellosolve, ethyl cellosolve, phenyl cellosolve, diethylene glycol monomethyl ether, propylene glycol monomethyl ether, dipropylene glycol monomethyl ether and tripropylene glycol monomethyl ether; and alcohols containing up to 8 carbon atoms. Mixtures of two or more solvents may also be used. Preferred examples of solvents include diethylene glycol, dipropylene glycol, diethylene glycol monomethyl ether, dipropylene glycol monomethyl ether and dimethylformamide, the most preferred solvent being diethylene glycol monomethyl ether.

When the composition is used for microbicidal/microbistatic purposes in various water systems, such as papermaking process water or industrial cooling water, it is preferable to employ a liquid preparation which uses the above-mentioned hydrophilic organic solvents and a dispersing agent, having regard to the solubility and dispersibility in water of the two active ingredients. Examples of dispersing agents include cationic, anionic, non-ionic or amphoteric surfactants, non-ionic surfactants being preferred. The non-ionic surfactants include higher alcohol-ethylene oxide (EO) adducts, alkylphenol-EO adducts, fatty acid-EO adducts, fatty acid polyhydric alcohol ester-EO adducts, alkylamine-EO adducts, fatty amide-EO adducts, fat-EO adducts, propylene oxide (PO)-EO copolymers, alkylamine PO-EO polymer adducts, fatty acid glycerol esters, fatty acid pentaerythrytol esters, fatty acid sugar esters, polyhydric alcohol alkyl esters and alkylolamides.

It is preferable to use higher alcohol-EO adducts, alkylphenol-EO adducts, fatty acid polyhydric alcohol ester-EO adducts, fatty amide-EO adducts, PO-EO copolymers, polyhydric alcohol alkyl ethers, alkylamine PO-EO copolymer adducts, alkylolamides and mixtures of two or more of these.

It is more preferable to use non-ionic surfactants, such as alkylamine PO-EO copolymer adducts (e.g. N,N,N',N'-polyoxyethylene-polyoxypropylene-ethylenediamine) and alkylolamides. The N,N,N',N'-polyoxyethylene-polyoxypropylene-ethylenediamines can be characterized as adducts of ethylenediamine and ethylene oxide-propylene oxide block copolymers and may be prepared by reacting ethylenediamine with propylene oxide and reacting the resultant intermediate adduct with ethylene oxide in accordance with conventional methods. Such surfactants may be represented by the following general formula:

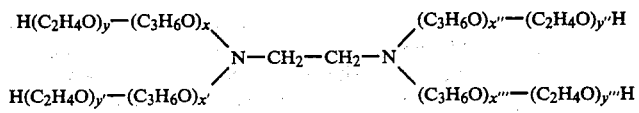

TETRONICS® (Wyandotte Chemical Corp., U.S.A.) and TETRONIC® (Asahi Denka Kogyo K.K., Japan) are commercially available products belonging to this class of surfactant.

In practising the present invention, use can be made of a wide variety of N,N,N',N'-polyoxyethylene-polyoxypropylene-ethylenediamines with variously different molecular weights, HLB (hydrophilic lipophilic balance) values, forms and other characteristics depending upon the amounts specified as desired of ethylene oxide and propylene oxide added respectively and on the manner of combination of these. Generally, however, those in which the total molecular weight of the propylene oxide units is about 2,000 to 27,000 and the ethylene oxide unit content is 10 to 80 percent by weight, based on the whole molecule, are preferably used.

Alkylolamide non-ionic surfactants are fatty acid alkylolamides synthesized from fatty acids and alkylolamines. It is preferable to use the alkylolamides obtained by reacting higher fatty acids containing 8 to 18 carbon atoms with ethanolamine or diethanolamine, those which are soluble in water being preferred. Especially preferred fatty acid alkylolamides are those obtained by reacting one mole of coconut oil fatty acid (a mixture of higher fatty acids derived from coconut oil) with one or two moles of diethanolamine. As commercially available products, there may be mentioned CONCENSATE P.A® (Continental Chemical Co., U.S.A.), STATOAMF® (Nippon Oil & Fats Co., Ltd., Japan) and PROFAN® (Sanyo Chemical Ind. Ltd., Japan).

According to circumstances (e.g. when a very high stability of the composition is not necessary), cationic, anionic or amphoteric surfactants may be used.

An appropriate total quantity of the hydrophilic organic solvent and dispersing agent is less than 99 parts (by weight) per 100 parts (by weight) of the composition. The composition usually contains 1 to 50 parts of 4,5-dichloro-1,2-dithiol-3-one and an alkylenebisthiocyanate and at least 0.01 part of the dispersing agent per part of the two active ingredients, the balance being the hydrophilic organic solvent. The quantity of the dispersing agent is preferably in the range of from 0.05 to 1.0 parts per part of the active ingredients.

The liquid composition may be prepared by conventional methods, for example by dissolving the active ingredients in the hydrophilic organic solvent and adding to it the surfactant, while stirring, to give a homogeneous solution. The order of dissolution and mixing may, of course, be reversed.

When the composition of the invention is used for microbicidal/microbistatic purposes in oils, such as heavy oil sludges, cutting oils or oily paints, it is preferably in the form of a liquid preparation using a hydrocarbon solvent, such as kerosene, heavy oil or spindle oil, and optionally containing an appropriate surfactant.

For use in microbicidal/microbistatic target materials in which the two active ingredients can be directly dissolved or dispersed, the active ingredients may be used as such or in the form of a powdery composition which is diluted with solid diluents (e.g. kaolin, clay, bentonite or carboxymethylcellulose) and optionally contains various surfactants.

The ratio of 4,5-dichloro-1,2-dithiol-3-one to 1,2-benzisothiazolin-3-one which produces a synergistic effect is usually about 8:1 to 1:128 by weight and preferably about 1:2 to 1:10.

The amount of composition added depends upon the target materials. For papermaking process water or industrial cooling water, additions of about 0.05 to 20 ppm will generally be adequate for inhibiting the growth of microbes (microbistatic use) and additions of about 0.05 to 50 ppm, preferably of about 1.0 to 30 ppm, will be adequate for microbicidal use. For microbicidal/microbistatic purposes of oils, additions of about several ppm to 250 ppm will generally be adequate.

According to one aspect of the present invention, there is provided a microbicidal/microbistatic method for industrial use, which comprises adding 4,5-dichloro-1,2-dithiol-3-one and 1,2-benzisothiazolin-3-one simultaneously, separately or at some time intervals, to the target materials to achieve a synergistic effect.

In the method according to the present invention, the simultaneous addition of the two active ingredients is conveniently made by using the above-mentioned compositions which contain both the active ingredients. However, separate compositions each containing one or other of the two active ingredients may be used, if desired, in certain cases. In these cases, liquid compositions are usually convenient.

Thus, for example, separate compositions for each of the two active ingredients may be prepared by dissolving any of the active ingredients in an appropriate organic solvent and optionally adding a dispersing agent to the resulting solution. In this case, because 4,5-dichloro-1,2-dithiol-3-one is easily hydrolyzed in the presence of water (as mentioned above), a composition using an anhydrous hydrophilic organic solvent of the above-mentioned type is preferable. On the other hand, the solvents for 1,2-benzisothiazolin-3-one can be anhydrous hydrophilic organic solvents, as well as water-containing organic solvents. If desired, it may be used in the form of an aqueous preparation. Non-ionic surfactants are appropriate for 1,2-benzisothiazolin-3-one, although other surfactants may be used.

In the case of target materials in which each of the two active ingredients can be directly dissolved or dispersed, the ingredients may be used as such or in the form of powdery compositions.

A specific example of a method for separately using the two active ingredients is first to add the 4,5-dichloro-1,2-dithiol-3-one to a system to be treated and then to add 1,2-benzisothiazolin-3-one to a certain specific part of the same system where the remarkable growth of microbes is recognized and a synergistic effect of the two active ingredients is desired. The level of addition and the ratio of the two active ingredients are as stated above.

The two active ingredients, when homogeneously dissolved or dispersed in the target materials, exert a potent synergistic microbicidal/microbistatic effect while retaining their respective antibacterial spectra. Accordingly, it is possible to save a significant quantity of the ingredients, compared with the single use of either of the two active ingredients.

The present invention is especially useful in providing a composition and a method for controlling slime which forms in process water in papermaking processes (e.g. in white water pipes or chest walls) or in cooling water in heat exchangers, drain channels and cooling towers of cycle-cooling systems. The composition and method can also be used for microbicidal/microbistatic purposes in liquid target materials, such as heavy oil sludges, cutting oils, lignin-containing waste liquors, various paints, latices and textile oils.

The following tests and Examples are given for the purpose of illustrating the present invention:

Test Method for Synergistic Effects

Synergistic effects were measured by the two-dimentional dilution method.

Definite quantities of solutions respectively containing two kinds of the test ingredients at known concentrations were added to a bouillon medium. The medium was inoculated with a definite quantity of a preculture of the test strain and incubated at 37° C. for 6.5 hours, while shaking. Concentrations of the respective ingredients at which no further increase in absorption at 660 nm was observed are called minimum inhibitory concentrations according to the two-dimensional dilution method (hereinafter abbreviated to TDMIC). FIG. 1 is a graphic representation of the TDMICs of two ingredients in a coordinate system [as usual but with such graduation that the minimum inhibitory concentrations of the respective ingredients used alone are expressed by an equal length on the respective axes]. In FIG. 1, the area above the curve (TDMIC curve) shows the growth inhibition area and the area below the curve is the growth area. Coincidence of the diagonal line with a TDMIC curve means a mere arithmetic addition of the actions; a TDMIC curve positioned over the diagonal line means an antagonistic action; and a curve positioned below the diagonal line expresses a synergistic effect.

EXAMPLE 1

(Psuedomonas aeruginosa)

Each of 4,5-dichloro-1,2-dithiol-3-one (hereinafter abbreviated Compound A) and 1,2-benzisothiazolin-3-one (abbreviated Compound B) was diluted 10 fold with dimethyl formamide as a solvent, starting from the dilution of 100 µg/ml. A synergistic effect was examined in accordance with the above-mentioned two-dimensional dilution method.

Figure 2:
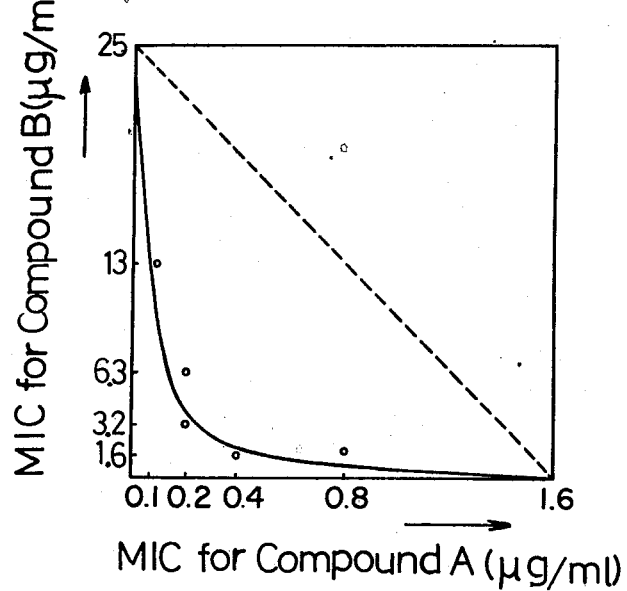
FIG. 2 is a graph of MIC against *Psuedomonas aeruginosa* of the microbicidal composition of the present invention, in accordance with the two-diminsional dilution method.

As shown in FIG. 2, the TDMIC curve clearly indicates a remarkable synergistic action against Psuedomonas aeruginosa and the optimum effect of the two compounds which completely inhibited the growth of bacteria is found at TDMICs of, for example, 0.2 µg/ml of Compound A and 3.2 µg/ml of Compound B. That is, each of these concentrations is about one eighth concentration as compared with the use of Compound A alone or Compound B alone, respectively. A strong synergistic effect has thus been demonstrated.

Other concentrations of A and B used together which produce a synergistic effect are shown in Table 1:

TABLE 1

| Concentration of Compound A, µg/ml | Concentration of Compound B, µg/ml |
| --- | --- |
| 0.2 (⅛) | 6.3 (¼) |
| 0.4 (¼) | 1.6 (1/16) |
| 0.4 (¼) | 3.2 (⅛) |
| 0.4 (¼) | 6.3 (¼) |

The figure in parenthesis is a ratio to the MIC value of Compound A or B alone.
The MIC for Compound A is 1.6 (µg/ml).
The MIC for Compound B is 25 (µg/ml).
Other combinations are referred to in FIG. 2.

EXAMPLE 2

(Bacillus subtilis)

Figure 3:
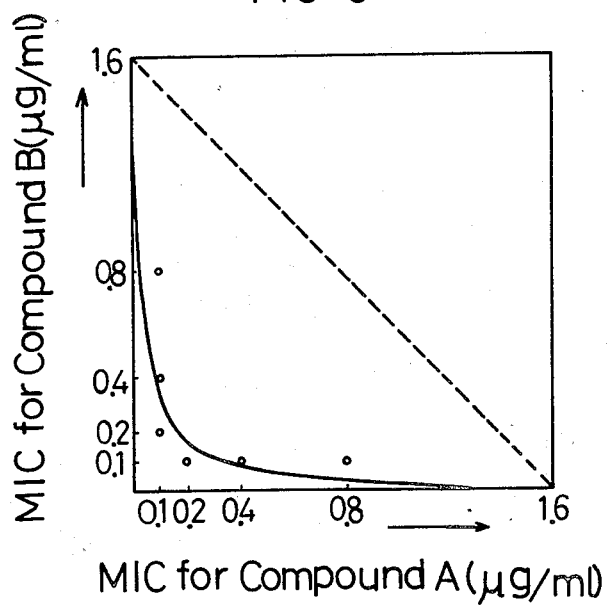
FIG. 3 is that against *Bacillus subtilis* and FIG. 4 is that against *Staphylococcus aureus.*

The result on Bacillus subtilis which was tested in the way similar to Example 1 is shown in Table 2 and FIG. 3.

TABLE 2

| Concentration of Compound A, µg/ml | Concentration of Compound B, µg/ml |
| --- | --- |
| 0.1 (1/16) | 0.2 (⅛) |
| 0.2 (⅛) | 0.1 (1/16) |
| 0.2 (⅛) | 0.2 (⅛) |
| 0.4 (¼) | 0.1 (1/16) |

The MIC for Compound A is 1.6 (µg/ml).
The MIC for Compound B is 1.6.
Others are referred to in FIG. 3.

EXAMPLE 3

(Staphylococcus aureus)

Figure 4:
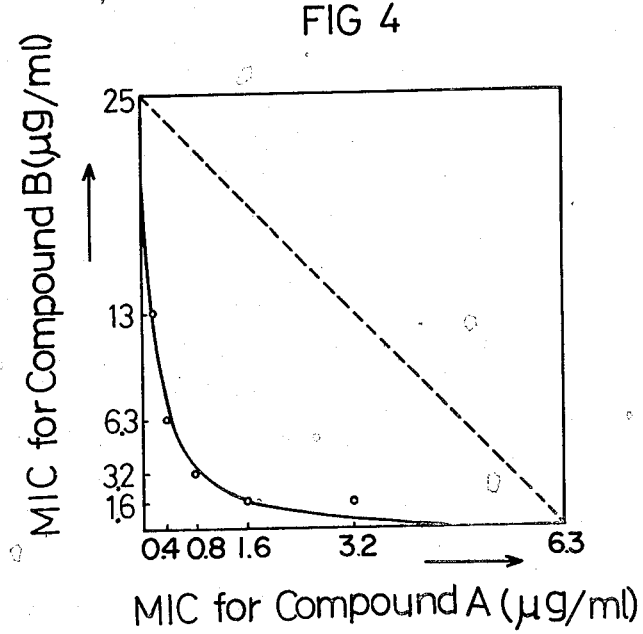

Similarly, the result on Staphylococcus aureus is shown in Table 3 and FIG. 4.

TABLE 3

| Concentration of Compound A, µg/ml | Concentration of Compound B, µg/ml |
| --- | --- |
| 0.4 (1/16) | 6.3 (¼) |
| 0.8 (⅛) | 3.2 (⅛) |
| 1.6 (¼) | 1.6 (1/16) |
| 1.6 (¼) | 3.2 (⅛) |

The MIC for Compound A is 6.3 (µg/ml).
The MIC for Compound B is 25.

Under the condition of each of Examples 1–3, the shaken culture was contained for 24 hrs and the remarkable synergistic action was sustained (which means that Compounds A and B are stable for each of the test strains).

EXAMPLE 4

For antiseptic purpose of cutting oil (which is used for cutting, drilling or polishing metals), the mixture of one part (by weight) of 4,5-dichloro-1,2-dithiol-3-one and eight parts of 1,2-benzisothiazolin-3-one was added to a cutting oil at the concentration of 5 ppm, which was allowed to stand in a humidistat at 30° C. and of 90% humidity. The change of numbers of viable bacteria in the test sample was observed with the passage of days. The result is shown in Table 4.

TABLE 4

| Days | The mixture 5 ppm | 4,5-Dichloro-1,2-dithiol 3-one 5 ppm | 1,2-Benzisothiazolin-3-one 5 ppm | No addition of ingredient |
| --- | --- | --- | --- | --- |
| 1 | <10 | <10 | $2.0 \times 10^2$ | $3.4 \times 10^{4*}$ |
| 7 | <10 | $7.3 \times 10^3$ | $3.2 \times 10^3$ | $5.3 \times 10^6$ |
| 15 | <10 | $5.3 \times 10^4$ | $5.7 \times 10^4$ | $2.8 \times 10^7$ |
| 30 | <10 | $2.6 \times 10^4$ | $4.1 \times 10^4$ | $4.2 \times 10^8$ |

*numbers of viable bacteria/ml.

The bacteria were cultured in bouillon agar medium.

EXAMPLE 5

For antiseptic purpose of an emulsive paint in can, the mixture of 1:10 (by weight) of 4,5-dichloro-1,2-dithiol-3-one and 1,2-benzisothiazolin-3-one was added at the concentration of 10 ppm and allowed to stand in the same way as in Example 4. The days for inhibiting putrefaction were tested. The result is shown in Table 5.

TABLE 5

| | The mixture 10 ppm | 4,5-Dichloro-1,2-dithiol-3-one 10 ppm | 1,2-Benzisothiazolin-3-one 10 ppm | No addition of ingredient |
| --- | --- | --- | --- | --- |
| Days for inhibition | >60 | 20 | 15 | 8 |

EXAMPLE 6

In a certain newsprint mill, the composition of 0.8% (w/w) 4,5-dichloro-1,2-dithiol-3-one, 99.0% of ethyleneglycol monomethylether and 0.2% of Tetronic 702 (a nonionic surfactant product) was added to the white water saveall pit of a paper making machine in a continuous manner for 6 hours a day such that a concentration in water of 10 ppm was obtained. At the 2nd week of the operation, slime mainly composed of bacteria was adhered to the inner walls of the flow box in the machine and break of paper occurred.

After washing the paper making machine with an alkali, the composition of 10.0% (w/w) of 1,2-benzisothiazolin-3-one, 89.8% of diethyleneglycol monomethylether and 0.2% Tetronic 702 was added in a continuous manner for 6 hours a day such that a concentration in water of 10 ppm was obtained. After one week, much slimes observed on the saveall part and the flow box part, and break of paper was found.

On the other hand, to the paper making machine after washing, the composition of 0.8% (w/w) of 4,5-dichloro-1,2-dithiol-3-one, 10.0% of 1,2-benzisothiazolin-3-one, 89.0% of diethyleneglycol monomethylether and 0.2% of Tetronic 702 was added for 6 hours a day such that 0.8 ppm of 4,5-dichloro-1,2-dithiol-3-one and 10 ppm of 1,2-benzisothiazolin-3-one in water were obtained. Even after 4 weeks of continuous operation, break of paper due to slime formation was not found, and thus the productivity was greatly improved.

What we claim is:

1. A microbicidal composition for industrial use comprising 4,5-dichloro-1,2-dithiol-3-one and 1,2-benzisothiazolin-3-one; the weight ratio of 4,5-dichloro-1,2-dithiol-3-one to the 1,2-benzisothiazolin-3-one being 8:1–1:128.

2. A composition according to claim 1, wherein the weight ratio is 1:2–1:10.

3. A method of killing or inhibiting the growth of bacteria, which comprises adding an antibacterial effective amount of a composition comprising 4,5-dichloro-1,2-dithiol-3-one and 1,2-benzisothiazolin-3-one process water of papermaking, industrial cooling water and to heavy oil sludges, cutting oils, and textile oils needing same; the weight ratio of 4,5-dichloro-1,2-dithiol-3-one to 1,2benzisothiazolin-3-one is 8:1–1:128.

4. A method according to claim 3, wherein the weight ratio is 1:2–1:10.

5. A method according to claim 3, wherein the bacteria are selected from the group consisting of *Psuedomonas aeruginosa, Bacillus subtilis* and *Staphylococcus aureus*.

* * * * *